(12) United States Patent
Higgs

(10) Patent No.: US 7,589,834 B2
(45) Date of Patent: Sep. 15, 2009

(54) DETECTION METHOD AND APPARATUS METAL PARTICULATES ON SEMICONDUCTORS

(75) Inventor: Victor Higgs, Hertfordshire (GB)

(73) Assignee: Nanometrics Incorporated, Milpitas, CA (US)

( * ) Notice: Subject to any disclaimer, the term of this patent is extended or adjusted under 35 U.S.C. 154(b) by 190 days.

(21) Appl. No.: 10/549,865

(22) PCT Filed: Apr. 8, 2004

(86) PCT No.: PCT/GB2004/001521
§ 371 (c)(1),
(2), (4) Date: Jul. 28, 2006

(87) PCT Pub. No.: WO2004/090516
PCT Pub. Date: Oct. 21, 2004

(65) Prior Publication Data
US 2006/0262296 A1 Nov. 23, 2006

(30) Foreign Application Priority Data
Apr. 9, 2003 (GB) ................... 0308182.5

(51) Int. Cl.
*G01N 21/00* (2006.01)
(52) U.S. Cl. .................................. 356/237.5
(58) Field of Classification Search .... 356/237.1–237.5
See application file for complete search history.

(56) References Cited

U.S. PATENT DOCUMENTS

| | | | |
|---|---|---|---|
| 3,841,927 A * | 10/1974 | Florence et al. | 438/567 |
| 3,998,668 A * | 12/1976 | Florence et al. | 148/22 |
| 4,246,793 A | 1/1981 | Fairand et al. | |
| 4,511,800 A * | 4/1985 | Harbeke et al. | 250/372 |
| 4,740,694 A | 4/1988 | Nishimura et al. | |
| 4,978,862 A | 12/1990 | Silva et al. | |
| 5,202,744 A | 4/1993 | Louis | |
| 5,244,820 A * | 9/1993 | Kamata et al. | 438/514 |

(Continued)

FOREIGN PATENT DOCUMENTS

JP 11-274257 10/1999

(Continued)

OTHER PUBLICATIONS

Bajaj, J. et al. (Jun. 1, 1993). "Spatially resolved characterization of HGCDTE materials and devices by scanning laser microscopy." *Semiconductor Science and Technology* 8(6S):872-877.

(Continued)

*Primary Examiner*—Tarifur R. Chowdhury
*Assistant Examiner*—Isiaka O Akanbi
(74) *Attorney, Agent, or Firm*—Silicon Valley Patent Group LLP

(57) ABSTRACT

A method of detecting surface particulate defects, and especially metal particulates, in semiconductors such as silicon, to characterise defects likely to have an effect on the electrical activity of such semiconductor materials, comprises exposing the surface of the semiconductor structure in the vicinity of a surface particulate to at least one high-intensity beam of light and collecting and processing the photoluminescence response; and using the result to identify unacceptable contamination levels resulting from diffusion of contaminant from particulate into semiconductor structure. Optionally, the semiconductor is annealed and photoluminescence responses collected before and after annealing to identify contaminant diffusion rates. Apparatus for the same is also described.

18 Claims, 3 Drawing Sheets

U.S. PATENT DOCUMENTS

| | | | | |
|---|---|---|---|---|
| 5,539,514 | A | * | 7/1996 | Shishido et al. .......... 356/237.4 |
| 5,659,187 | A | | 8/1997 | Legoues et al. |
| 5,995,217 | A | | 11/1999 | Watanabe |
| 6,075,592 | A | | 6/2000 | Banerjee et al. |
| 6,108,079 | A | | 8/2000 | Maeshima et al. |
| 6,160,615 | A | | 12/2000 | Matsui et al. |
| 6,214,560 | B1 | * | 4/2001 | Yguerabide et al. ............ 506/3 |
| 6,251,754 | B1 | * | 6/2001 | Ohshima et al. ............ 438/506 |
| 6,256,092 | B1 | | 7/2001 | Tomita et al. |
| 6,429,968 | B1 | | 8/2002 | Carver |
| 6,462,817 | B1 | | 10/2002 | Strocchia-Rivera |
| 6,628,111 | B2 | * | 9/2003 | Shapiro et al. ............ 324/71.2 |
| 6,893,936 | B1 | | 5/2005 | Chen et al. |
| 6,911,347 | B2 | | 6/2005 | Higgs |
| 7,113,276 | B1 | | 9/2006 | Higgs et al. |
| 7,139,083 | B2 | | 11/2006 | Fielden et al. |
| 7,140,202 | B2 | * | 11/2006 | Freund et al. ................ 65/17.2 |
| 7,245,696 | B2 | | 7/2007 | Yun et al. |
| 7,306,951 | B1 | * | 12/2007 | Benson et al. ............. 436/144 |
| 2002/0054295 | A1 | * | 5/2002 | Maris ......................... 356/496 |
| 2002/0088952 | A1 | | 7/2002 | Rao et al. |
| 2002/0119485 | A1 | | 8/2002 | Morgan |
| 2003/0061212 | A1 | | 3/2003 | Smith et al. |
| 2003/0094579 | A1 | | 5/2003 | Hasegawa et al. |
| 2004/0092042 | A1 | | 5/2004 | Higgs |
| 2004/0252297 | A1 | | 12/2004 | Fairley et al. |
| 2006/0281281 | A1 | | 12/2006 | Tanzawa et al. |
| 2007/0000434 | A1 | | 1/2007 | Buczkowski |
| 2007/0007466 | A1 | | 1/2007 | Laurent et al. |
| 2007/0008518 | A1 | | 1/2007 | Hummel et al. |
| 2007/0008526 | A1 | | 1/2007 | Buczkowski |
| 2007/0176119 | A1 | | 8/2007 | Hummel |

FOREIGN PATENT DOCUMENTS

| | | |
|---|---|---|
| JP | 11-354599 | 12/1999 |
| JP | 2000-193597 A | 7/2000 |
| JP | 2003-045928 A | 2/2003 |
| WO | WO-98/11425 A1 | 3/1998 |
| WO | WO-02/29883 A1 | 4/2002 |
| WO | WO 02/29883 A1 * | 4/2002 |
| WO | WO-02/077621 A1 | 10/2002 |
| WO | WO-2004/010121 A1 | 1/2004 |
| WO | WO-2004/090516 A1 | 10/2004 |
| WO | WO-2007/005438 A2 | 1/2007 |
| WO | WO-2007/005438 A3 | 1/2007 |
| WO | WO-2007/008311 A2 | 1/2007 |
| WO | WO-2007/008399 A2 | 1/2007 |
| WO | WO-2007/008399 A3 | 1/2007 |
| WO | WO-2007/008430 A2 | 1/2007 |
| WO | WO-2007/008430 A3 | 1/2007 |

OTHER PUBLICATIONS

Bellone, S. et al. (1991). "Recombination measurement of n-type heavily doped layer in high-low silicon junctions," *IEEE Trans. Electron. Devices* 38(3):532-537.

Commere, B. et al. (Sep. 1988). "Control of the fabrication steps of InP MIS transistors by means of scanning photoluminescence measurements," *Journal de Physique*, Colloque, Paris, France 49(C-4)(Suppl. 9): 431-436.

Derbyshire, K. (Summer 2004). "The engineered substrate's balancing act: performance gains versus greater costs and increased yield risks," *Yield Management Solutions Magazine* located at http://www.kla-tencor.com/company/magazine/summer04/coverstory.pdf. pp. 29.

DiStefano, T.H. et al. (Feb. 1987). "Non-destructive, non-contacting test of Si wafers by thermore-flectance," *IBM Technical Disclosure Bulletin*, 10 pages.

Fitzgerald, E.A. et al. (Nov. 3, 1998). "Dislocations in relaxed SiGe/Si heterostructures," MIT Department of Materials Science and Engineering and AmberWave Technologies, pp. 227-238.

Higgs, V et al. (Feb. 15, 1993), "Characterization of compositionally graed Si1-xGex alloy layers by photoluminescence spectroscopy and by cathodoluminescence spectroscopy and imaging," *Journal of Applied Physics* 73(4):152-156.

Higgs, V. (2000). "Characterization of Si, SiGe, and SOI structures using photoluminescence," *Materials Research Society Symposium Proceedings* 588:129-140.

Higgs, V. et al. (Sep. 13, 1999). "Application of room temperature photoluminescence for the characterization of impurities and defects in silicon," *Proceedings of SPIE* 3895:21-37.

Korsunska, N.E. et al. (Jul. 2004). "High temperature photoluminescence spectroscopy in p-type SiC," *Semiconductor Science and Technology* 19(7):833-838.

Miner, C.J. (1992), "Non-destructive, whole wafer assessment of optoelectronic epitaxial materials," *Semicond. Sci. Technol.* 7:A10-A15.

Montangero, P. et al. (May 1, 1994). "Optical-beam-induced current and photoluminescence techniques for localization of crystallographic defects in optoelectronic devices," *Materials Science and Engineering B* B24(1/03):175-179.

Moore, C.J.L. et al. (Jun. 1990), "A spatially resolved spectrally resolved photoluminescence mapping system," *J. Crystal Growth* 103(1/4):21-27.

Pritchard, R.E. et al. (Jun. 1, 1993). "Composition assessment by spatially resolved photoluminescence of INGAAS and INGAASP epilayers grown on recessed INP substrates," *Semiconductor Science and Technology* 8(6):1166-1172.

Ressel, P. et al. (1993). "Optimized proton implantation step for vertical-cavity surface-emitting lasers," *Electron. Lett.* 29(10):918-919.

Ribes, A.C. et al. (May 1, 1995), "Photoluminescence imaging of porous silicon using a confocal scanning laser macroscope/microscope," *Applied Physics Letters* 66(18):2321-2323.

Tajima, M. (1990), "Characterization of semiconductors by photoluminescence mapping at room temperature," *Journal of Crystal Growth* 130:1-7.

Tajima, M. et al. (1990), "Mapping of microdefects in silicon crystals by photoluminescence at room temperature," Semiconductor Silicon 1990 from *Proceedings of the Sixth International Symposium on Silicon Materials Science and Technology*, eds. H. R. Huff et al., Electrochem. Soc., Inc.: Pennington, NJ, pp. 994-1004.

Titus, J. (Jun. 1, 2004). "Keep an eye on wafer defects," *Test & Measurement World* located at http://www.reed-electronics.com/tmworld/article/CA420488.html, 5 pages.

Westrate, S. et al. (Feb. 2002). "Photoluminescence mapping detects CU contamination in SI wafers," *Solid State Technology* 45(2):57-58.

"RPM2000 Rapid Photoluminescence Mapper," Sales Brochure, Date Unknown, 6 pages.

"SPHER: The key to revealing hidden problems in Siwafers," Sales Brochure, Date Unknown, 8 pages.

Office Action mailed on Jan. 5, 2000 for U.S. Appl. No. 09/254,521, filed Mar. 8, 1999 by Higgs et al., 6 pages.

Response to Office Action mailed on Sep. 19, 2005 for U.S. Appl. No. 09/254,521, filed Mar. 8, 1999 by Higgs et al., 14 pages.

Notice of Allowance mailed on May 18, 2006 for U.S. Appl. No. 09/254,521, filed Mar. 8, 1999 by Higgs et al., 14 pages.

Restriction Requirement mailed on Jun. 14, 2007 for U.S. Appl. No. 11/177,735, filed Jul. 8, 2005 by Buczkowski, 6 pages.

Response to Restriction Requirement mailed on Jul. 23, 2007 for U.S. Appl. No. 11/177,735, filed Jul. 8, 2005 by Buczkowski, 16 pages.

Office Action mailed on Sep. 12, 2007 for U.S. Appl. No. 11/177,735, filed Jul. 8, 2005 by Buczkowski, 42 pages.

Office Action mailed on Oct. 3, 2007 for U.S. Appl. No. 11/426,877, filed Jun. 27, 2006 by Hummel et al., 8 pages.

Response to Office Action mailed on Dec. 20, 2007 for U.S. Appl. No. 11/426,877, filed Jun. 27, 2006 by Hummel et al., 10 pages.

Ex Parte Quayle Action mailed on Jun. 11, 2007 for U.S. Appl. No. 11/427,080, filed Jun. 28, 2006 by Laurent et al., 6 pages.

Request for Continued Examination and Amendment mailed on Aug. 10, 2007 for U.S. Appl. No. 11/427,080, filed Jun. 28, 2006 by Laurent et al., 5 pages.

Office Action mailed on Oct. 10, 2007 for U.S. Appl. No. 11/427,080, filed Jun. 28, 2006 by Laurent et al., 7 pages.

International Search Report mailed on Dec. 18, 1997 for PCT Application No. PCT/GB97/02388 filed Sep. 5, 1997 by Bio-Rad Micromeasurements, Ltd, 2 pages.
International Search Report mailed on Aug. 31, 2007 for PCT Application No. PCT/US06/25083 filed on Jun. 27, 2006 by Accent Optical Technologies, Inc., 4 pages.
International Search Report mailed on Oct. 1, 2007 for PCT Application No. PCT/US06/24938 filed on Jun. 27, 2006 by Accent Optical Technologies, Inc., 4 pages.
International Search Report mailed on Sep. 4, 2007 for PCT Application No. PCT/US06/25257 filed on Jun. 28, 2006 by Nanometrics, Inc., 2 pages.
International Search Report mailed on Jul. 22, 2004 for PCT Application No. PCT/GB2004/001521 filed on Apr. 8, 2004 by AOTI Operating, Inc., 4 pages.
Ivanov, I.G. et al., "Donor doping calibration in 4H-SiC using photoluminescence spectroscopy", IEEE 1996, 0-7803-3179-6/96 pp. 223-226.
Response to Office Action dated Feb. 12, 2008 for U.S. Appl. No. 11/177,735, filed Jul. 8, 2005 by Buczkowski, 22 pgs.
Office Action mailed on Jun. 23, 2008, for U.S. Appl. No. 11/177,735, filed Jul. 8, 2005 by Buczkowski, 33 pages.
Office Action mailed on Jun. 2, 2008, for U.S. Appl. No. 11/343,500, filed Jan. 30, 2006 by Hummel (32 pgs).
Response to Office Action filed Mar. 27, 2008, for U.S. Appl. No. 11/427,080, filed Jun. 28, 2006 by Laurent et al., (6 pgs).
Notice of Allowance mailed on Jun. 5, 2008 for U.S. Appl. No 11/427,080, filed Jun. 28, 2006 by Laurent et al. (10 pgs).
Notice of Allowance mailed on May 1, 2008 for U.S. Appl. No. 11/528,723, filed Sep. 26, 2006 by Higgs et al., 7 pages.
RCE and IDS mailed on Jul. 10, 2008 for U.S. Appl. No. 11/528,723, filed Sep. 26, 2006 by Higgs et al., 4 pages.
Notice of Allowance mailed on Aug. 18, 2008 by Examiner Michelle R. Cushwa Connelly for U.S. Appl. No. 11/528,723, filed Sep. 26, 2006 by Higgs et al., 7 pages.
RCE and IDS mailed on Jul. 10, 2008 for U.S. Appl. No. 11/528,723, filed Sep. 26, 2006 by Higgs et al., 5 pages.
Request for Continued Examination and IDS mailed on Aug. 28, 2008 for U.S. Appl. No. 11/427,080, filed Jun. 28, 2006 by Laurent et al., 5 pages.
Notice of Allowance mailed on Sep. 23, 2008 for U.S. Appl. No. 11/528,723, filed Sep. 26, 2006 by Higgs et al., 11 pages.
Notice of Allowance mailed on Sep. 19, 2008, for U.S. Appl. No. 11/426,877, filed Jun. 27, 2006 by Hummel et al., 6 pages.
Notice of Allowance mailed on Aug. 8, 2008, for U.S. Appl. No. 11/426,877, filed Jun. 27, 2006 by Hummel et al., 7 pages.
Request for Continued Examination mailed on Sep. 4, 2008, for U.S. Appl. No. 11/426,877, filed Jun. 27, 2006 by Hummel et al., 4 pages.
Notice of Allowance mailed on Sep. 12, 2008 for U.S. Appl. No. 11/427,080, filed on Jun. 28, 2006 by Laurent et al., 9 pgs.
Office Action mailed on Dec. 11, 2007, for U.S. Appl. No. 11/528,723, filed Sep. 26, 2006 by Higgs, 7 pgs.
Response to Office Action mailed Jan. 30, 2008, for U.S. Appl. No. 11/528,723, filed Sep. 26, 2006, by Higgs, 15 pgs.

* cited by examiner

| Figure 1a. Before Heating Micro Scan (0.12 x 0.06 mm) | Figure 1b After Heating at 250°C (0.12 x 0.06 mm) |
|---|---|
|  |  |
| Figure 2a. Before Heating Micro Scan (0.12 x 0.06 mm) | Figure 2b After Heating at 250°C (0.12 x 0.06 mm) |
|---|---|
| 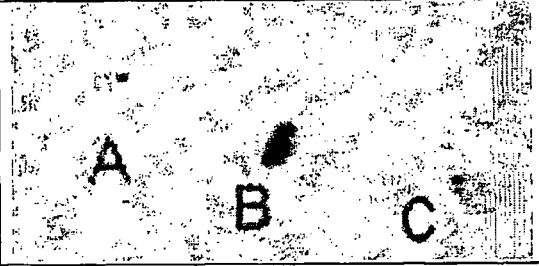 | 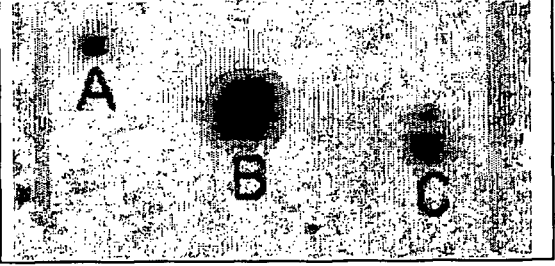 |
| Figure 3a. After Heating at 400°C (10 x 10 mm) | Figure 3b. After Heating at 400 C (10 x 10 mm) |
|---|---|
| 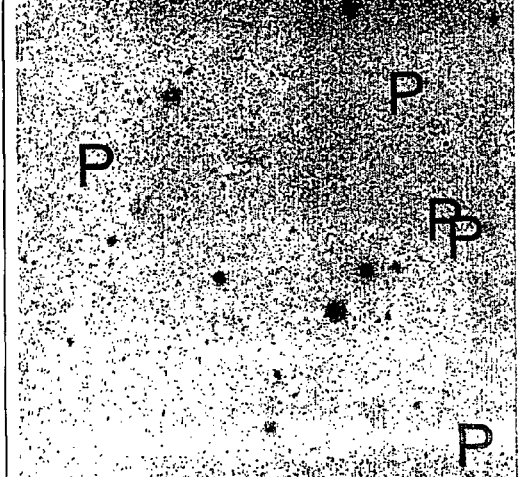 | 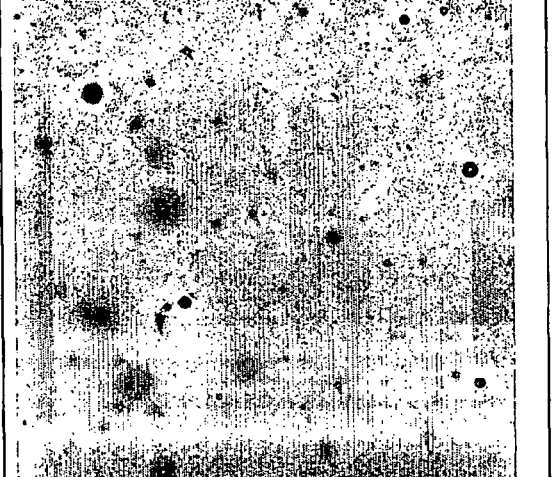 |

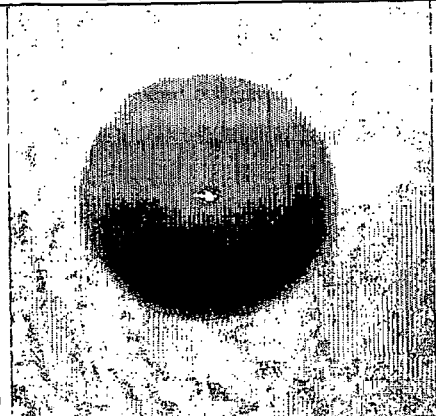 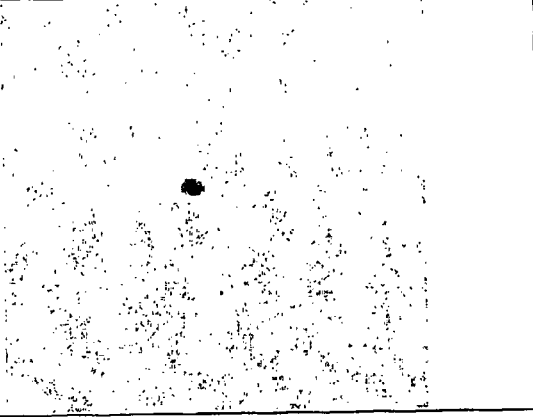
Figure 4a. After Heating at 400°C PL Image (0.28 x 0.28 mm)
Figure 4b. After Heating at 400°C Surface Map Image (0.28 x 0.28 mm)

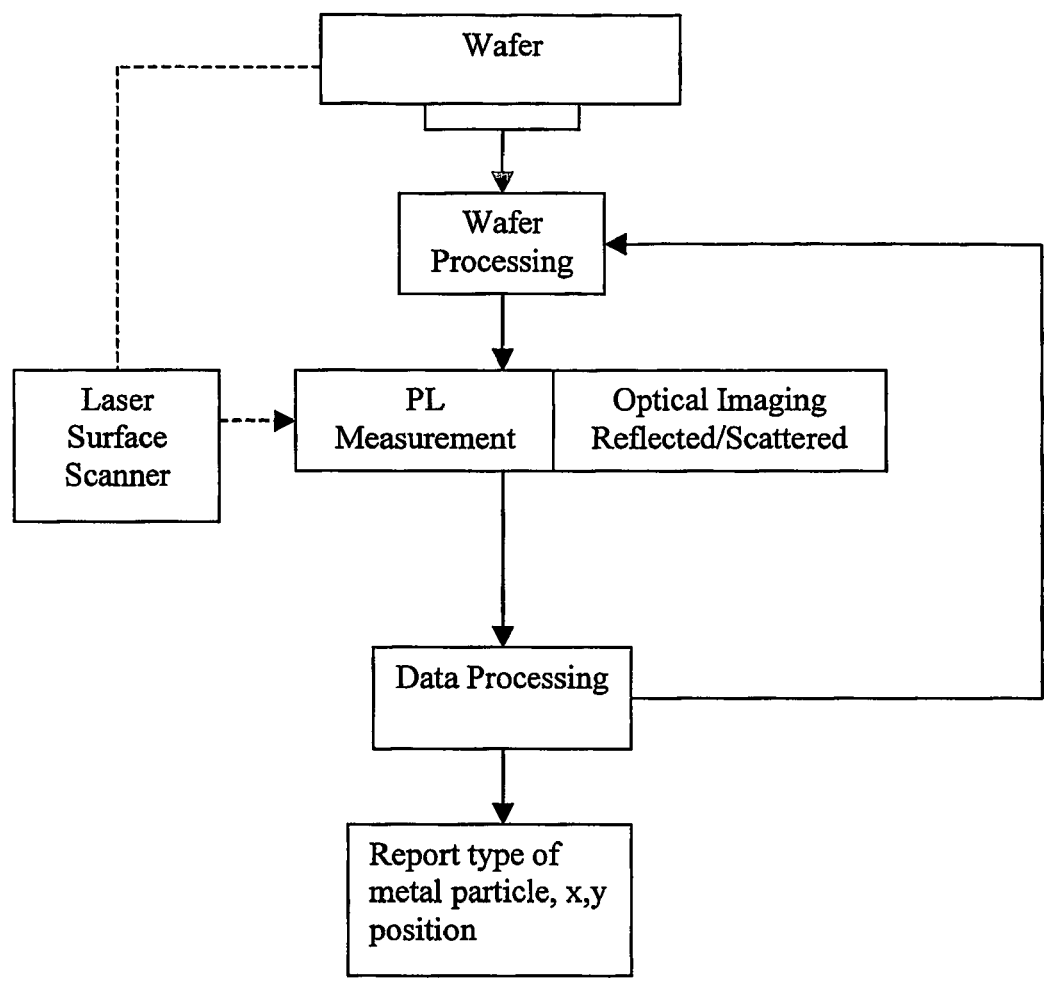
Figure 5. Measurement Process Flowchart

DETECTION METHOD AND APPARATUS METAL PARTICULATES ON SEMICONDUCTORS

CROSS-REFERENCES TO RELATED APPLICATIONS

This application is a U.S. National Phase application of PCT/GB2004/001521, filed 8 Apr. 2004, the entirety of which is incorporated herein by reference. This application also claims the benefit of British Patent Application No. 0308182.5 filed 9 Apr. 2003.

BACKGROUND

The invention relates to method and apparatus for detecting surface particulate defects, and especially metal particulates, in semiconductors such as silicon. The invention in particular relates to an improved method and apparatus to characterise defects likely to have an effect on the electrical activity of such semiconductor materials, and consequently a deleterious effect on the behaviour devices fabricated therefrom.

DETAILED DESCRIPTION

Surface particles in semiconductor processing are a major cause of degradation of device performance and device yield loss. Contaminate particles can locally mask lithographic, implant or etch steps which can cause shorts or open circuit. Also such particles can degrade the gate oxide integrity, which degrade the operation of all (MOS) Metal oxide semiconductor devices. Particles, with characteristic dimensions such as a fraction of the chip's smallest features can lead to killer defects.

The critical size for a technology has historically been one half or one third of the gate length for a MOS device. As semiconductors get smaller and smaller, copper is seen as a better choice for interconnects because it is a better conductor than aluminium. The tendency of copper from interconnects to diffuse into the surrounding chip material, poisoning the silicon or other semiconductor material, has largely been overcome by modifying the deposition step to first deposit a barrier material lining the etched tracks, onto which the copper is deposited, sealed by further barrier material deposition.

However, particles generated during processing can inadvertently contaminate a wafer. As with any semiconductor-manufacturing step, control of surface particles is therefore critical. It is customary to measure particulate addition to a wafer after a process step and also after surface cleaning. Location and quantification of particles on a wafer surface is accomplished using a laser surface scanner, which detects the scattered light from surface particles. The wafer surface is excited with a focused laser beam and reflected and scattered light is collected using a number of different detectors placed at different angles relative to the excitation direction. Surface particles scatter the light in all directions away from the specular reflection direction. The particle density is detected by scattered light pulses, as the laser is scanned across the wafer. The particle size is detected through the size dependence of the scattered light and determined using calibrated standard particle sizes.

There is a lower limit to the particle size that can be detected, because of the wafer surface roughness. The surface itself has a certain amount of scattered light and if the particle scatter falls within the surface scatter it cannot be detected. New laser scanning systems angle resolved measurements could overcome this limitation. The current international specification for particles is defined as one-half of the design technology: for a 190 nm device process this would be $\geq 90$ nm particles, with a density $\leq 0.18$ cm$^{-2}$.

If the particle size is smaller than the qualification specification it will not be detected during particle detection. However metal particles can be present on the wafer surface that are within the current particle specification but which after processing can diffuse into the semiconductor material and have a potentially detrimental effect on the device performance, leading to enhanced leakage and gate oxide degradation.

Laser surface scanners detect all types of particles, such as organic, non-metallic and metallic. The detection of small metallic particles (below the current detection limit) that are on the surface of the wafer or are diffused into the wafer is becoming critical for device processes using Cu interconnects. Therefore it is important to monitor incoming wafers for metallic particles, as well as device-processed wafers. In addition monitor wafers are used to detect particles in device processes equipment such as a furnace or metal etcher, and this type of wafer would need to be assessed.

It is an object of the present invention to develop a method and apparatus for detecting surface particulate defects, and especially metal particulates, in semiconductors such as silicon which mitigates some or all of the above disadvantages.

It is a particular object of the invention to provide a method and apparatus for detecting such surface particulate defects at sizes below current particulate qualification specifications.

It is a particular object of the invention to provide a method and apparatus for characterising such surface particulate defects in a manner that relates at least to some extent to their effect on the electrical activity of the semiconductor rather than to size alone.

Thus, in accordance with the present invention in its first aspect a method of detecting surface particulate defects, and especially metal particulates, in semiconductors such as silicon, and in particular of characterising defects likely to have an effect on the electrical activity of such semiconductor materials, comprises the steps of:

exposing the surface of the semiconductor structure in the vicinity of a surface particulate to at least one high-intensity beam of light from a suitable light source, preferably a laser, and in particular a high-intensity laser;

collecting photoluminescence produced by excitation of the semiconductor structure by the light beam;

processing the collected photoluminescence to produce a result representative of the intensity of the photoluminescence response;

using the result to detect and characterise surface particulate defects, and especially metal particulates, in semiconductors such as silicon, and in particular characterise defects likely to have an effect on the electrical activity of such semiconductor materials, for example by then comparing the result with suitable reference data and for example a predetermined acceptable specification range of photoluminescence to identify unacceptable contamination levels resulting from diffusion of contaminant from particulate into semiconductor structure.

The photoluminescence technique produces a spatially resolved PL map at a resolution determined by the characteristics of the high-intensity beam of light. This can be exploited by further preferred features of the present method, but for the fundamental objective of the invention is to resolve this map to a level capable of producing a result indicating the PL intensity over the wafer area in the vicinity of a surface particulate and thus obtain useful information about the level of contamination, and consequent likely detriment to electrical activity.

Photoluminescence (PL) spectroscopy is a very sensitive technique for investigating both intrinsic and extrinsic electronic transitions at impurities in semiconductors. When silicon is excited with laser irradiation above the band-gap of the material, electron hole pairs are produced. These carriers can recombine in various different ways, some of which give rise to luminescence. The electron hole pairs can be trapped at impurities in silicon and they emit photons characteristic of this interaction, thereby giving impurity specific information in the photoluminescence spectra. The spectra are inherently indicative of the electrical activity of the semiconductor material in the vicinity of the particulates, being indicative therefore of the effect on this electrical activity of diffusion of contaminant from the particulates into the semiconductor wafer, such as might occur during fabrication even from particulates smaller than current specification. Thus, in accordance with the method a result related to the deleterious changes to electrical activity in the region of a particulate is obtained, allowing direct detection of such problems rather than indirect screening relying on particulate size considerations.

This photoluminescence result can then be used to characterise the defect and/or the likely detrimental effect on electrical activity by making a comparison of the result with previously obtained results, for example from a semiconductor sample with known defects and/or known sample performance. For example the photoluminescence result can then be compared to a predetermined acceptable specification range developed in association with studies using more precise analysis methods (e.g. electrical yield test methods on the fabricated device). In a refinement of the method, a final step comprises making a quality classification of the semiconductor structure based upon such a comparison, and in particular rejecting or selecting for remedial action semiconductor structures exhibiting a photoluminescence response outside the said predetermined acceptable specification range.

It has generally been accepted in order to obtain this spectral information and unambiguous chemical identification of the optical centres, measurements need to be carried out at liquid helium temperatures. It is known throughout the industry that at room temperature the PL signal is significantly weakened and very little useful spectral information can be obtained. However, International patent application WO98/11425, which describes a non-destructive technique that makes practical the detection of electrically active defects in semiconductor structures based on room temperature PL. That reference discloses a PL technique which has industrial application in that it enables the image to be produced within minutes and which has a further added advantage in producing micro imaging of small individual defects particularly near to the surface of the wafer, where the device is fabricated.

A room temperature PL technique is accordingly preferred, such as in particular that described by WO98/11425. Moreover, the particular effectiveness of this technique in identifying copper contamination in near-surface semiconductor structures has been described in International patent application WO02/29883. Preferred features of the methods described in those applications and incorporated herein by reference will be understood to be applicable to the present invention. The present invention relies on the surprising realisation that these methods can be used not merely to detect lattice contamination inherent in the semiconductor structure for the reasons set out in those references, but is also singularly effective in detecting contamination arising from diffusion of contaminant from surface particulates into the semiconductor structure, and is accordingly singularly effective in providing information about the effect of such particulates in practice which is more relevant to ultimate device performance than direct particulate measurement methods such as those based on particulate size alone.

The success of the room temperature PL method disclosed in the above references is, in part, due to the probing volume probed by the laser being small, spatial resolution preferably 0.1 to 20 µm, ideally 2 to 5 µm, and with a peak or average power density of between $10^4$ to $10^9$ watts/cm$^2$, so that localised contaminants have much greater effect on the measured PL intensity and is also believed, in part, because since the excitation is focused the injected carrier density is high.

The light beam used to generate the PL effect is so controlled, and in particular beam power and/or wavelength and/or spot size so controlled, as to identify defects at a selective depth in said semiconductor structure, so as to collect PL information from a suitable near-surface depth reflecting the level at which the device is fabricated. Typically this might for example be from the upper 12 µm of the semiconductor structure. For certain materials and devices, smaller depths may be appropriate, down to for example 5 µm or even 1 µm. In particular the light beam used to generate the PL effect is a high-intensity laser.

Reference herein to a high-intensity laser is meant to include, without limitation, a high power density laser i.e. where regardless of the power of the laser the emittance is focused.

In order to perform the method of the invention effectively, it is necessary to locate particulates posing a potential problem and then to obtain the PL information characteristic of electrical activity of contamination in the vicinity thereof, to give an indication of whether diffusion from the particulate into the surface is a problem. In a preferred embodiment therefore the method comprises a first step of locating surface particulates using a suitable particulate imaging method, and a subsequent or simultaneous second step of generating PL intensity information as above described from the vicinity of each particulate to provide a quantification of the extent to which contaminant has diffused from the particulate into the near-surface region of the semiconductor, in particular to an extent where the level of contaminant will be detrimental to device performance.

The basic PL technique can be used to generate a PL map imaging the PL response across the whole wafer. This is not likely to be the most rapid alternative in practice. The particulate imaging, mapping and locating method might conveniently alternatively be by another suitable method. This might involve the generation of a scattered light dark field image and/or a reflected light bright field image.

In the former case the method might for example be a conventional laser surface scanning method as above described or another suitable relatively rapid scanning method. In the latter case the method comprises generation of a reflected light surface map of the area under test, preferably simultaneously with the PL image and using the same light source.

That is, the method includes the steps of:

directing a high intensity beam of light such as a high-intensity laser at a surface of a sample of semiconductor structure to be tested in the manner above described;

producing a first or photoluminescence image from photoluminescence produced by excitation of the semiconductor structure by the light beam;

producing a second image mapping the location of the particulates, either as a dark field image of light scattered from the surface of the semiconductor structure or as a bright field image of light reflected from the surface of the semiconductor structure;

using the second image to detect and map surface particulates;

processing the photoluminescence image to produce a result representative of the intensity of the photoluminescence response of the semiconductor structure in the vicinity of the surface particulates so detected;

for example then comparing the result with a predetermined acceptable specification range of photoluminescence.

The second image may be produced from light from the same primary light source as that generating the PL image, or from an additional high intensity light source, in which latter case the additional light source is preferably a laser source, such as a conventional laser scanner, and the method comprises directing a second high intensity beam of light such as a high-intensity laser at a surface of a sample of semiconductor structure to be tested simultaneously or successively with the first high intensity beam of light, respectively to generate the said particulate map image and the said PL response.

Comparison of the first and second images to identify target particulates may be merely by simultaneous observation. Preferably however the images are analysed statistically, for example by digitizing prior to performing a numerical comparison/analysis.

Preferably, the method involved generating a digitized intensity measurement (e.g. point by point reading but preferably a digitized intensity map) representative of the intensity of the first, PL image; generating a digitized intensity measurement (e.g. point by point reading but preferably a intensity digitized map) representative of the intensity of the second image; numerically processing the digitized intensity measurements to produce the result above.

A suitable detailed example of such a method is described in International Application No WO 02/077621.

The PL image and the corresponding reflected surface image or other map which is equivalent to an optical microscope image may be recorded. Surface particles are detected in reflected image. Only after contaminant from the surface particle has diffused into the wafer (and the contamination is now in the Si or other semiconductor crystal lattice) are metal-related defects produced which are electrically active. These metal related defects are now observed in the PL map because they are electrically active. Therefore it is easy to identify areas for investigation by inspecting and comparing the PL and surface image recorded at the same location.

The preferred PL technique of the present invention is capable of generating a spatially resolved PL map across the area of the wafer. In the primary method of the invention, PL intensity data is collected for each particulate which is compared with reference data to make the quality control decision. If the method is to be used for such a go-no go quality control decision then only the PL level associated with a particulate is of concern. Coarse scanning by another more rapid method to locate particulates is used as above.

Nevertheless, it is a particular advantage of the technique of the present invention that it can additionally be used to generate a spatially resolved map of PL signals across the surface of the semiconductor under test, and in particular to generate a spatially resolved image of those signals. Accordingly, in a preferred embodiment, the method further comprises the step of generating such a map and/or such an image.

In these circumstances, it can be appropriate to work to mapping/imaging resolutions of 0.5 mm or less across the entire wafer. It might for example be appropriate to use such more detailed map generation on a batch sampling basis.

If the wafer is annealed this would diffuse contaminant from the particle into the wafer and make their detection easier. Accordingly, in a preferred embodiment of the method, the semiconductor material is first heated to anneal and effect such diffusion prior to carrying out the detection steps as above. This might again be more suited to a batch testing process for quality control.

Heating of the semiconductor material may be effected by any suitable process, for example by incorporating heating means into any carrier apparatus. Heating to temperatures of between 200 and 400° C. can be suitable to encourage more rapid diffusion of target species and create the desired annealing effect. Alternatively, the annealing effect might be produced inherently, particularly during device processing, for species with high diffusion rates at lower temperature.

Copper in particular diffuses very rapidly at low temperatures, as compared to other metallic impurities. Therefore if wafer was heated prior to analysis, the main effect observed should due especially to Cu. The method is in particular a method of detecting contamination from copper surface particulates, and in this example of the method the optional heating step is particularly useful.

The result from the annealed sample may again be used to detect and characterise surface particulate defects, and especially metal particulates, in semiconductors such as silicon, and in particular characterise defects likely to have an effect on the electrical activity of such semiconductor materials, for example by then comparing the result with a predetermined acceptable specification range of photoluminescence to identify unacceptable contamination levels resulting from diffusion of contaminant from particulate into semiconductor structure.

Moreover, diffusion rates vary between species. This allows a further refinement of the invention. The detection steps may be repeated and a photoluminescence result collected prior to and subsequent to an annealing step and the results compared to determine the difference and obtain an indication of rates of diffusion so as to identify the contaminant.

In a further alternative the invention thus comprises a first step of collecting photoluminescence produced by excitation of the semiconductor structure by the light beam and processing the collected photoluminescence to produce a first photoluminescence result representative of the intensity of the photoluminescence response as above described;

a heating step as above described to anneal the sample;

a second step of collecting photoluminescence produced by excitation of the semiconductor structure by the light beam and processing the collected photoluminescence to produce a second photoluminescence result representative of the intensity of the photoluminescence response as above described after annealing;

a step of comparing the results of each photoluminescence step to determine the difference and obtain an indication of rates of diffusion so as to identify the contaminant.

Again, the comparison between first and second photoluminescence results is preferably performed numerically, for example by digitizing photoluminescence information collected at each stage prior to performing a numerical comparison/analysis with reference to known diffusion data for likely contaminant species.

In accordance with a further aspect of the invention an apparatus for detecting surface particulate defects, and especially metal particulates, in semiconductors such as silicon, and in particular for characterising defects likely to have an effect on the electrical activity of such semiconductor materials, comprises means to perform the foregoing method.

In a particular example the apparatus therefore comprises a support for a semiconductor sample under test; a high intensity light source, preferably a laser, and in particular a high-intensity laser; means to focus a high intensity beam of light from the light source onto a surface of a semiconductor sample under test on the support; collection means to collect photoluminescence data produced by excitation of the semiconductor structure by the light beam at least in the vicinity of particulates on the surface thereof; means to process the collected data to produce a result representative of the intensity of the photoluminescence response in the said vicinity; preferably also a comparator to compare the result with suitable reference data and for example a predetermined acceptable specification range of photoluminescence to identify unacceptable contamination levels resulting from diffusion of contaminant from particulate into semiconductor structure.

Preferably the apparatus further includes means to locate particulates on the surface of the semiconductor structure, and in particular imaging means to create an image map of such location, simultaneously with the PL signal or otherwise. This might be a scattered light dark field image and/or a reflected light bright field image.

In the former case the imaging means might for example be a conventional laser surface scanner as above described with suitable collection optics or another suitable relatively rapid scanning method. In the latter case imaging means are provided to enable the creation of a reflected light surface map of the area under test, preferably simultaneously with the PL image using the same light source.

For example the apparatus includes a first imaging means to produce a first image from photoluminescence produced by excitation of the semiconductor structure by the light beam; a second imaging means to produce a second image of the surface of the semiconductor structure mapping particulates thereon, either as a dark field image of light scattered from the surface of the semiconductor structure or as a bright field image of light reflected from the surface of the semiconductor structure; an image processor to process the second image to detect and map surface particulates and to process the first image to produce a result representative of the intensity of the photoluminescence response of the semiconductor structure in the vicinity of the surface particulates so detected; and a comparator to compare the result with a predetermined acceptable specification range of photoluminescence.

The second image may be produced from light from the same primary light source as that generating the PL effect, or from an additional light source, in which latter case the additional light source is preferably a laser source, such as a conventional laser scanner.

The imaging means may include a display (direct screen, photographic, camera and screen etc) allowing simultaneous viewing by an observer. Additionally or alternatively, digital imagers such as digital cameras collect digitised image intensity data to be processed numerically as above described.

In further preferred embodiment of the invention the light source of the apparatus comprises a laser of a spot size of between 0.1 mm and 0.5 microns and/or a power density of between $10^4$ to $10^9$ watts/cm$^2$.

Preferably the apparatus further includes means to heat the sample under test to produce the annealing effect above described. In one alternative therefore, the apparatus is an apparatus for detecting surface particulate defects, and especially metal particulates, in semiconductors such as silicon, to characterise defects likely to have an effect on the electrical activity of such semiconductor materials, and comprises a support for a semiconductor sample under test; a high intensity light source; means to focus a high intensity beam of light from the light source onto a surface of a semiconductor sample under test on the support; collection means to collect photoluminescence data produced by excitation of the semiconductor structure by the light beam at least in the vicinity of particulates on the surface thereof; means to process the collected data to produce a result representative of the intensity of the photoluminescence response in the said vicinity; heating means to heat the sample in situ, allowing a photoluminescence response to be measured before and after heating, and a comparator to compare the said two photoluminescence responses to determine the difference and obtain an indication of rates of diffusion so as to identify the contaminant.

In particular heating means are associated with the support. For example the support comprises a heated stage.

Other preferred apparatus features will be appreciated by analogy with the foregoing description of the method.

BRIEF DESCRIPTION OF THE DRAWINGS

The invention is illustrated with reference to FIGS. 1 to 5 of the accompanying drawings in which:

FIGS. 1 to 4 show various images produced by an apparatus in accordance with the invention;

FIG. 5 is a schematic representation of an implementation of the invention.

FIG. 1a shows a PL image revealing an area containing of surface metal particle induced contamination. After low temperature heating at 250° C. (See FIG. 1b) the defect contrast and the size of the area effected by the contamination have increased. The similar type of effect is shown in FIGS. 2a-2b. This is attributed to diffusion of the metal particle into the Si wafer.

Copper can diffuse into a Si wafer a room temperature, and it can diffuse through the wafer thickness (≈625 um) from the wafer backside to the wafer front in 4 hours. Clearly any contamination on the backside caused by handling could be transferred to the wafer front surface and effect the devices fabricated in this region.

As noted, copper diffuses very rapidly at relatively low temperatures, as compared to other metallic impurities. Therefore if the wafer was heated prior to analysis in accordance with the invention, the main effect observed should due especially to Cu. Also when low levels of Cu are diffused into the crystal lattice this can cause an increase in the local PL signal (previous SiPHER Cu patent) and can be used to identify Cu metallic particles diffused into the wafer.

The effect of the intentional Cu particle induced contamination was also investigated. The wafers were annealed at 400° C. for 30 minutes to increase the diffusion of the metal contamination into the wafer, enhancing the defective area contrast. FIG. 3a-3b show large area scans revealing the contamination effect by the surface particles. These defects are shown as having halo effects or moon like features (see defects labelled P in FIGS. 3a-3b). These particles induced defective areas cover between 200-600 μm. The wafer could then mapped to produce a wafer map. The particle enhanced diffused areas could be readily identified.

A micro scan recorded at high resolution (as shown in FIG. 4a-4b) reveals the effect of particle diffusion into the wafer. The PL micro map and the corresponding surface image reveal the particle in the centre of the scanned area.

By measuring the image after controlled heating it would be possible to get information on the nature of the metal diffusing. Since each metal has a well known diffusion constant in Si, by heating the wafer for a fixed time and temperature and measuring the SiPHER image before and after heating an indication of the potential type of metal contamination can be obtained.

$$L=\sqrt{4tD}$$

D=Diffusion coefficient at heating temperature (cm$^2$/s)

L=Diffusion length (cm)

T=Time (Seconds)

For example heating at a temperature of 1050° C., for 1 hour. Cu can diffuse up to 12 mm, compared to 2 mm for Fe and about 0.007 mm for Ti.

Metal particle defects could be detected by using different heating methods and chemical treatments used in a typical device process, such as furnace oxidation, rapid thermal processing (RTP). Also an in-situ hot wafer chuck, or halogen lamp could be used. Alternatively laser heating could be used, either employing the light source used for the PL effect and/or particulate imaging as above described, or from a yet further dedicated source. These could all be part of the system.

Also the particles could be detected using a laser surface scanner as part of the hardware. The particles could be inspected directly in the same hardware configuration using the measurement optics described for example in the prior art patent applications referred to hereinabove.

Also wafer maps can be recorded on the wafer backside. This helps to identify whether the source of the contamination came from the wafer back surface.

FIG. 5 is a measurement process flowchart illustrating a possible implementation of the invention.

The invention claimed is:

1. A method of detecting surface particulate defects, and especially metal particulates, in semiconductors such as silicon, to characterise defects likely to have an effect on the electrical activity of such semiconductor materials, comprises the steps of:
    annealing a semiconductor structure to diffuse contaminants from a surface particulate into the semiconductor material;
    after annealing the semiconductor structure, exposing the surface of the semiconductor structure in the vicinity of a surface particulate to at least one high-intensity beam of light from a suitable light source;
    collecting photoluminescence produced by excitation of the semiconductor structure by the light beam;
    processing the collected photoluminescence to produce a result representative of the intensity of the photoluminescence response;
    comparing the result with a predetermined acceptable specification range of photoluminescence to identify unacceptable contamination levels resulting from diffusion of contaminants from the surface particulate into the semiconductor structure.

2. A method in accordance with claim 1 as a method of quality control comprising a further step of making a quality classification of the semiconductor structure based upon such a comparison, and rejecting or selecting for remedial action semiconductor structures exhibiting a photoluminescence response outside the said predetermined acceptable specification range.

3. A method in accordance with claim 2 further comprising a prior step of determining a predetermined acceptable specification from studies of samples of fabricated devices using electrical yield test methods.

4. A method in accordance with claim 1 wherein the exposing, collecting and processing steps are performed prior to and subsequent to the annealing step and the results compared to determine the difference and obtain an indication of rates of diffusion so as to identify the contaminant.

5. A method of detecting surface particulate defects, and especially metal particulates, in semiconductors such as silicon, to characterise defects likely to have an effect on the electrical activity of such semiconductor materials, comprises:
    a first step of collecting photoluminescence by:
        exposing the surface of the semiconductor structure in the vicinity of a surface particulate to at least one high-intensity beam of light from a suitable light source;
        collecting photoluminescence produced by excitation of the semiconductor structure by the light beam;
        processing the collected photoluminescence to produce a first photoluminescence result representative of the intensity of the photoluminescence response;
    a heating step to the semiconductor to diffuse contaminant from the particle into the semiconductor material;
    a second step of collecting photoluminescence produced by like method to the first to produce a second photoluminescence result representative of the intensity of the photoluminescence response as above described after annealing;
    a step of comparing the results of each photoluminescence step to determine the difference and obtain an indication of rates of diffusion so as to identify the contaminant.

6. A method in accordance with claim 5 wherein the light source is a high-intensity laser.

7. A method in accordance with claim 6 wherein the spatial resolution of the laser is 0.1 to 20 μm.

8. A method in accordance with claim 6 wherein the laser provides a peak or average power density of between $10^4$ to $10^9$ watts/cm$^2$.

9. A method in accordance with claim 5 wherein the light beam used to generate the PL effect is so controlled as to collect PL information from no deeper than the upper 12 μm of the semiconductor structure.

10. A method in accordance with claim 5 comprising a first step of locating surface particulates using a suitable particulate imaging method, and a subsequent or simultaneous second step of generating PL intensity information in accordance with any preceding claim from the vicinity of each particulate to provide a quantification of the extent to which contaminant has diffused from the particulate into the near-surface region of the semiconductor.

11. A method in accordance with claim 10 wherein the particulate imaging, mapping and locating method comprises the generation of a scattered light dark field image and/or a reflected light bright field image.

12. A method in accordance with claim 11 including the steps of:
    directing a high intensity beam of light such as a high-intensity laser at a surface of a sample of semiconductor structure to be tested in the manner above described;
    producing a first or photoluminescence image from photoluminescence produced by excitation of the semiconductor structure by the light beam;

producing a second image mapping the location of the particulates, either as a dark field image of light scattered from the surface of the semiconductor structure or as a bright field image of light reflected from the surface of the semiconductor structure;

using the second image to detect and map surface particulates;

processing the photoluminescence image to produce a result representative of the intensity of the photoluminescence response of the semiconductor structure in the vicinity of the surface particulates so detected.

13. An apparatus for detecting surface particulate defects, and especially metal particulates, in semiconductors such as silicon, to characterise defects likely to have an effect on the electrical activity of such semiconductor materials, comprises a support for a semiconductor sample under test; means to heat the sample under test associated with the support to diffuse contamination from a particulate into a semiconductor structure of the sample under test; a high intensity light source; means to focus a high intensity beam of light from the light source onto a surface of a semiconductor sample under test on the support; collection means to collect photoluminescence data produced by excitation of the semiconductor structure by the light beam at least in the vicinity of particulates on the surface thereof; means to process the collected data to produce a result representative of the intensity of the photoluminescence response in the said vicinity; a comparator to compare the result with a predetermined acceptable specification range of photoluminescence to identify unacceptable contamination levels resulting from diffusion of contaminant from particulate into semiconductor structure.

14. An apparatus in accordance with claim 13 wherein the means to heat the sample under test associated with the support comprises a heated stage.

15. An apparatus for detecting surface particulate defects, and especially metal particulates, in semiconductors such as silicon, to characterise defects likely to have an effect on the electrical activity of such semiconductor materials, comprises a support for a semiconductor sample under test; a high intensity light source; means to focus a high intensity beam of light from the light source onto a surface of a semiconductor sample under test on the support; collection means to collect photoluminescence data produced by excitation of the semiconductor structure by the light beam at least in the vicinity of particulates on the surface thereof; means to process the collected data to produce a result representative of the intensity of the photoluminescence response in the said vicinity; heating means to heat the sample in situ, allowing a photoluminescence response to be measured before and after heating, and a comparator to compare the said two photoluminescence responses to determine the difference and obtain an indication of rates of diffusion so as to identify the contaminant.

16. An apparatus in accordance with claim 15 wherein the heating means comprises a heated stage.

17. An apparatus in accordance with claim 16 further including imaging means to create an image map of the location of particulates on the surface of the semiconductor structure.

18. An apparatus in accordance with claim 17 wherein the imaging means generates a scattered light dark field image and/or a reflected light bright field image.

* * * * *

UNITED STATES PATENT AND TRADEMARK OFFICE
CERTIFICATE OF CORRECTION

| | | |
|---|---|---|
| PATENT NO. | : 7,589,834 B2 | Page 1 of 1 |
| APPLICATION NO. | : 10/549865 | |
| DATED | : September 15, 2009 | |
| INVENTOR(S) | : Victor Higgs | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 463 days.

Signed and Sealed this

Fourteenth Day of December, 2010

David J. Kappos
*Director of the United States Patent and Trademark Office*